United States Patent [19]
Eveleth et al.

[11] Patent Number: 5,622,981
[45] Date of Patent: Apr. 22, 1997

[54] USE OF METABOTROPIC RECEPTOR AGONISTS IN PROGRESSIVE NEURODEGENERATIVE DISEASES

[75] Inventors: David D. Eveleth, Mission Viejo; Judith A. Kelleher, Irvine; Carl W. Cotman, Santa Ana, all of Calif.

[73] Assignee: Cortex Pharmaceuticals, Inc., Irvine, Calif.

[21] Appl. No.: 418,903

[22] Filed: Apr. 7, 1995

Related U.S. Application Data

[63] Continuation of Ser. No. 70,518, Jun. 1, 1993, abandoned.

[51] Int. Cl.⁶ .......................... A61K 31/195; A61K 31/42
[52] U.S. Cl. ............................................. 514/380; 514/561
[58] Field of Search ...................................... 514/380, 561

[56] References Cited

U.S. PATENT DOCUMENTS

| | | |
|---|---|---|
| 5,028,622 | 7/1991 | Plaitakis .................................. 514/561 |
| 5,135,956 | 8/1992 | Borg et al. ............................... 514/724 |
| 5,158,976 | 10/1992 | Rosenberg .............................. 514/561 |

FOREIGN PATENT DOCUMENTS

| | | |
|---|---|---|
| WO8907098 | 8/1989 | WIPO . |
| WO92/03137 | 8/1991 | WIPO . |

OTHER PUBLICATIONS

Abstract, "β–Amyloid Peptide Potentiates Quisqualate Toxicity in HT–4 Neuronal Cell Line", Kelleher, Estrada and Eveleth, 24th Annual Meeting for Amer. Soc. for Neurochem., VA, Mar. 1993.
"A Metabotropic Glutamate Receptor Agonist Does Not Mediate Neuronal Degeneration in Cortical Culture", Koh, Palmer, Line and Cotman, Brain Res., 561 (1991) 338–343.
"Acetylcholine and Glutamate Mediate Fast Excitation; GABA and Glycine Mediate Fast Inhibition", Ligand–gated Ion Channels and Fast Synaptic Transmission, Chap. 19, The Nervous System, 1083–1084 no date.
"Learning in the Mammalian Hippocampus Depends on $Ca^{2+}$ Entry Through a Doubly Gated Channel", Non–Channel–linked Receptors and Synaptic Modulation, Chap. 19, The Nervous System, 1099–1100, no date.
"62 –Amyloid Increases Neuronal Susceptibility to Injury by Glucose Deprivation", Copani, Koh and Cotman, Neuropharmacology and Neurotoxicology NeuroReport 2, 763–765 (1991).
"Activation of Metabotropic Receptors Has a Neuroprotective Effect in a Rodent Model of Focal Ischaemia", Chiamulera, Alebertini, Valerio and Reggiani, European J. of Pharmacology, 216 335–336 (1992).
"Metabotropic Excitatory Amino Acid Receptors Reveal Their True Colors", TiPS, Oct. 1991, vol. 12, 365–367.
"β–Amyloid Protein Increases the Vulnerablity of Cultured Cortical Neurons to Excitotoxic Damage", Koh, Yang and Cotman, Brain Research, 533 (1990), 315–320.

"Activation of the Metabotropic Glutamate Receptor Attenuates N–Methyl–D–Aspartate Neurotoxicity in Cortical Cultures", Proc. Natl. Acad. Sci. USA, vol. 88, Nov. 1991, Neurobiology, 9431–9435.
Neuroscience Facts, FIDIA Res. Foundation, Sep. 1992, vol. 3, No. 17, 65–68.
"Vintage Amino Acid Meeting Describes New Tools for Amino Acid Research, Subtypes of Metabotropic Receptors", Henley and Johnston, Meeting Rpt., TiPS, vol. 12, Oct. 1991, 357–359.
"β–Amyloid Stimulates Glial Cells In Vitro to Produce Growth Factors that Accumulate in Senile Plaques in Alzheimer's Disease", Araujo and Cotman, Brain Research, 569 (1992) 141–145.
"Preservation of 5–Hydroxytryptamine$_{1A}$ Receptor–G Protein Interactions in the Cerebral Cortex of Patients with Alzheimer's Disease" O'Neill et al., Neuroscience Letters, 133 (1991) 15–19.
"Glutamate Neurotoxicity and Diseases of the Nervous System", Dennis W. Choi, Neuron, vol. 1, Oct. 1988 623–634.
"Systemic Administration of MK–801 Protects Against Ischemia–Induced Hippocampal Neurodegeneration in the Gerbil", Foster and Woodruff, The Journal of Neuroscience, Oct. 1987 3343–3349.
"Pharmacological Protection Against the Toxicity of N–Methyl–D–Aspartate In Immature Rat Cerebellar Slices", A. Lehmann, Neuropharmacology, vol. 26, No. 12, 1751–1761 (1987).
"Blockade of N–Methl–D–Aspartate Receptors May Protect Against Ischemic Damage in the Brain", Science, vol. 226, 850–852 (1984).
"Abusive Stimulation of Excitatory Amino Acid Receptors: A Strategy to Limit Neruotoxicity", Manev et al., The FASEB Journal, vol. 4 Jul. 1990, 2789–2797 no date.
"Glutamate Neurotoxicity Is Independent of Calpain In Inhibition in Primary Cultures of Cerebellar Granule Cells", Manev, et al., Journal of Neurochemistry, vol. 57, No. 4, 1288–1295 1991.
"Desensitization of Metabotropic Glutamate Receptors in Neuronal Cultures", Catania, et al., Journal of Neurochemistry, vol. 56, No. 4 1329–1335 1991.
"Abstract #72" 18th International Joint Conference on Stroke and Cerebral Circulation, p. 179, no date.

(List continued on next page.)

Primary Examiner—José G. Dees
Assistant Examiner—B. Bembenick
Attorney, Agent, or Firm—Townsend and Townsend and Crew LLP

[57] ABSTRACT

A method of treating a mammal with a neurodegenerative disease which is caused at least in part by the neurotoxic effects of the β-amyloid protein. This method constitutes administering a metabotropic receptor agonist to such a mammal. In particular, the agonist trans-ACPD or 1S,3R-ACPD can be administered intravenously to treat a mammal with Alzheimer's disease.

18 Claims, 1 Drawing Sheet

OTHER PUBLICATIONS

Silprandi, Renata, et al. (1992) "Activation of the glutamate metabotropic receptor protects retina against N–methyl–D–aspartate toxicity", *European Journal of Pharmacology*, 219:173–174.

Dewar, D., et al. (1991) "Glutamate metabotropic and AMPA binding sites are reduced in Alzheimer's disease: an autoradiographic study of the hippocampus", *Brain Research*, 553:58–64.

Nakamura, Yu, et al., (1992) "Amyloid β–protein precursor deposition in rat hippocampus lesioned by ibotenic acid injection", *Neuroscience Letters*, 136:95–98.

Baskys, A., (1991) "Agonists at Metabotropic Glutamate Receptors Presynaptically Inhibit EPSC's In Neonatal Rat Hippocampus", *Journal of Physiology*, 444:687–701.

*The Merck Index* (1989), Merck & Co., Rahway, NJ, USA; see page 775, No. 4808: Ibotenic acid.

USE OF METABOTROPIC RECEPTOR AGONISTS IN PROGRESSIVE NEURODEGENERATIVE DISEASES

This is a continuation Ser. No. 08/070,518, filed Jun. 1, 1993, now abandoned.

FIELD OF THE INVENTION

The present invention relates to a method of treating neurodegenerative diseases which are caused at least in part by the neurotoxic effects of the β-amyloid protein. This method includes the administration of a metabotropic receptor agonist to patients who have or who are at risk for contracting neurodegenerative diseases, particularly progressive neurodegenerative diseases such as Alzheimer's disease. Specifically, the metabotropic receptor agonist ACPD has been found to be effective in treating such conditions.

BACKGROUND OF THE INVENTION

1. The Glutamatergic System

The amino acids glutamate and aspartate are known to function as excitatory neurotransmitters in the mammalian central nervous system. These amino acids activate a large series of excitatory receptors known as "glutamate receptors". These receptors, along with the various neurotransmitters which activate them, in turn make up the glutamatergic system, the dominant excitatory nerve impulse transmission system of the mammalian central nervous system.

Over the last few years, it has come to be recognized that the overstimulation of excitatory neurotransmitter receptors can have serious pathological consequences. The overstimulation of cultured neurons invitro by glutamate, for example, can lead to neuronal cell death. Excitotoxicity is now thought to be important in the pathogenesis of several neurodegenerative disorders, including stroke and ischemic injury.

2. The Glutamate Receptors

Both pharmacological and molecular studies have revealed that glutamate receptors comprise a large family of proteins with extensive heterogeneity at the molecular level. The different classes of glutamate receptors differ in both their preferred pharmacological ligands and in their functions.

At least three classes of glutamate receptors have been identified. One of these, the NMDA class of receptors, is specifically activated by the glutamate analog N-methyl-D-aspartate. When stimulated, NMDA receptors open ion channels and allow an influx of cations into a neuron. The non-NMDA receptors comprise another group of ionotropic receptors which mediate cation flow into neurons.

A third class of glutamate receptors which has been identified is known as the metabotropic class of receptors. These receptors are referred to as "metabotropic" because their stimulation does not result directly in the opening of an ion channel, as is the case with the NMDA and non-NMDA ionotropic glutamate receptors. Instead, the cellular effects caused by the stimulation of a metabotropic receptor are mediated by G-proteins. The metabotropic receptors can be pharmacologically distinguished from other types of glutamate receptors in that they are specifically stimulated by trans-ACPD (aminocyclopentane 1,3-dicarboxylic acid). No other known glutamate receptors are stimulated by trans-ACPD.

At least four types of metabotropic receptors have now been described (see Henley, J. M. and Johnston, G. A. R., *Trends in Pharmacological Sci*, 12:357–360 (1991)). Metabotropic receptors are found in nerve cells of the central nervous system both presynaptically and postsynaptically, and are also found in glial cells. In vitro, metabotropic receptors have been shown to mediate slow depolarization of hippocampal neurons. It has also been found that metabotropic receptors block spike accommodation, a slow hyper-polarization following the excitation of a neuron which limits its ability to fire action potentials. Thus, the activation of the metabotropic receptors can render neurons more excitable (see Miller, Richard J., *Metabotropic excitatory amino acid receptors reveal their true colors*, TIPS, 12:365–367 (1991)).

3. β-Amyloid Protein and Alzheimer's Disease

Alzheimer's Disease (AD) is a progressive neurodegenerative disease which is histologically characterized by an accumulation of neuritic plaques and neurofibrillary tangles and by neuron cell death. A major component of these neuritic plaques is the β-amyloid protein, which is derived from a precursor protein called the β-amyloid precursor protein (APP). The β-amyloid protein itself has been shown to be toxic to neurons in vitro.

The β-amyloid protein has, moreover, also been shown to potentiate the cytotoxicity caused by the overstimulation of glutamate receptors. When mature neuron cultures are exposed to doses of β-amyloid that are too low to cause neuronal degeneration by themselves and are then subsequently exposed to sublethal doses of glutamate, massive cell death occurs. In addition to potentiating the toxicity of glutamate, β-amyloid has been shown to increase the toxicity to neurons of exposure to NMDA and kainate, which are agonists of non-metabotropic glutamate receptors (Koh, J., et al., *β-Amyloid protein increases the vulnerability of cultured cortical neurons to excitotoxic damage*, Brain Research, 553:315–320 (1990)).

There is also evidence that β-amyloid exposure specifically makes neurons more susceptible to injury or death due to the stimulation of non-NMDA glutamate receptors. The addition of 100 μM of a synthetic β-amyloid peptide to a neuron cell culture which had previously been exposed to quisqualate (an agonist of metabotropic receptors and also other glutamate receptors) caused a threefold increase in the release of LDH (lactate dehydrogenase, an indicator of cell damage) by the neurons in the culture. Even at higher concentrations of quisqualate, we have observed greater cell death when neurons are exposed to the β-amyloid peptide compared to when they are exposed to quisqualate alone.

SUMMARY OF THE INVENTION

In accordance with one aspect of the present invention, methods of treating neurodegenerative disease are disclosed and described. One embodiment of this aspect of the invention involves a method of treating a mammal with a neurodegenerative disease which is caused at least in part by β-amyloid protein neurotoxicity, comprising administering to the mammal a pharmacologically effective dose of a metabotropic receptor agonist. Metabotropic receptor agonists include agents which can act selectively as an agonist at a metabotropic receptor and not at a receptor in the ionotropic class of glutamate receptors, including, for example, ACPD. The metabotropic receptor agonist ibotenate, however, can also be used. This embodiment of the present invention is useful in treating such neurodegenerative diseases as Parkinson's disease and Alzheimer's disease.

Another aspect of the present invention involves a method of preventing a neurodegenerative disease in a mammal which has at least one of the indicia of the disease, wherein the disease is caused at least in part by the neurotoxic effects of the β-amyloid protein, comprising administering a pharmacologically effective dose of a metabotropic receptor agonist to the mammal. Metabotropic receptor agonists which can be used in this embodiment also include agents which can act selectively as an agonist at a metabotropic receptor and not at a receptor in the ionotropic class of glutamate receptors, including for example, ACPD. Ibotenate, however, can also be used in this embodiment. This method is useful in particular in the treatment of mammals who have or are at risk of developing Parkinson's disease or Alzheimer's disease.

A further aspect of the present invention involves a method of treating nervous system cells which are exposed to β-amyloid protein, comprising contacting the cells with a dose of a metabotropic receptor agonist which is effective in preventing or treating damage to the cells caused by the exposure of the cells to β-amyloid protein. The cells can be mammalian nervous system cells, and the cells can be treated in vivo. Alternatively, the nervous system cells can be treated in vitro. Metabotropic receptor agonists useful in treating cells of the nervous system include, for example, ACPD and ibotenate.

DETAILED DESCRIPTION OF THE INVENTION

Figure 1:
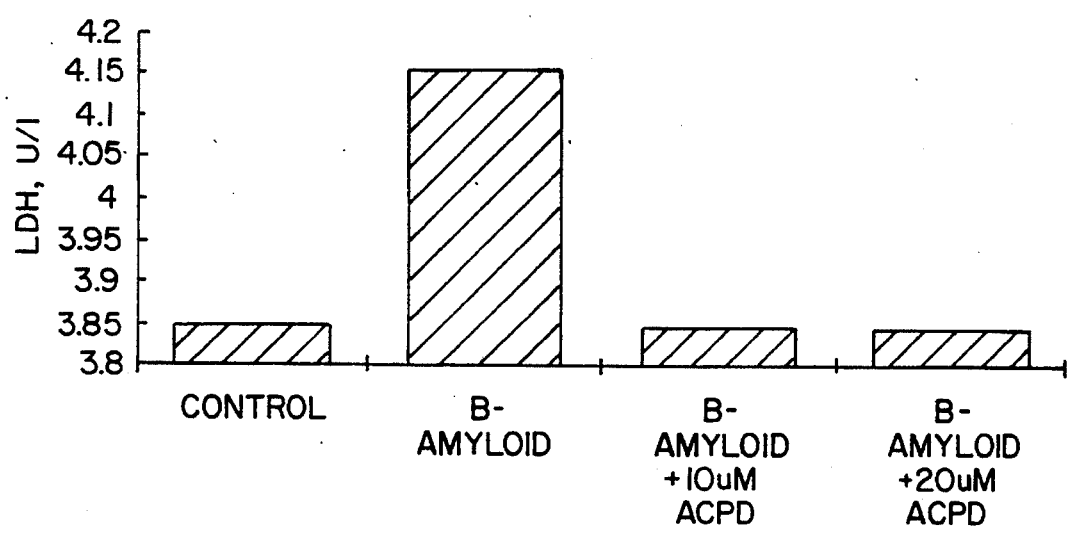
FIG. 1 is a graph depicting the results of an experiment in which cultured embryonic rat hippocampal neurons were exposed to β-amyloid protein either alone or in combination with ACPD.

The prior art shows that the stimulation of metabotropic receptors, like other glutamate receptors, causes the depolarization of neurons and renders them more susceptible to further excitation. It is further known that the β-amyloid protein potentiates the excitotoxicity caused by the stimulation of glutamate receptors. One of skill in the art would thus predict that the stimulation of metabotropic receptors in the presence of the β-amyloid protein would cause an increase in cellular damage and in the amount of neuron cell death.

It is one of the surprising findings of the present invention, however, that stimulating metabotropic receptors with agonists of these receptors in fact protects neurons from death or injury when such neurons are exposed to the β-amyloid protein. This finding is completely unexpected in light of prior art teachings that the excitotoxicity of glutamate receptor agonists, including agonists which stimulate metabotropic receptors, is potentiated by the β-amyloid protein. Another finding of the present invention is that metabotropic receptor agonists can be used to treat neurons which have already been exposed to β-amyloid proteins. Thus, neurodegenerative diseases caused by β-amyloid toxicity can be treated or prevented by administering metabotropic agonists to subjects who suffer from or are at risk for contracting a neurodegenerative condition associated with β-amyloid toxicity.

The most widespread disease associated with β-amyloid toxicity is Alzheimer's disease (AD). A subject who is at risk for acquiring Alzheimer's disease or who is already afflicted with that disease can thus be effectively treated with a metabotropic receptor agonist. Metabotropic receptor agonists can be used to substantially prevent Alzheimer's disease or to help to cure a subject who already has this disease. In addition, other β-amyloid-associated neurodegenerative diseases, such as Hereditary Cerebral Hemorrhage with Amyloidosis-Dutch Type (HCHWA-D), can also be so treated.

Other neurodegenerative diseases which are not known to be associated with β-amyloid exposure can be exacerbated if not necessarily solely caused by β-amyloid toxicity. Thus, metabotropic receptor agonists can also be effectively used in the treatment of neurodegenerative diseases besides those directly associated with β-amyloid toxicity. For example, such diseases as Parkinson's disease, ALS, Huntington's Disease, Multiple Infarct Dementia, and Transigent Ischemic Attack (TIA) can be treated. Thus, a method of treating neurodegenerative diseases besides AD and HCHWA-D is also within the scope of the invention.

As used herein, the terms "metabotropic receptors" and "metabotropic receptor" refer to those glutamate receptors which are activated specifically by trans-ACPD and 1S,3R-ACPD, are G protein linked, and do not directly mediate the opening of ion channels in neuron cell membranes. Other as yet uncharacterized glutamate receptors which are similarly G protein linked and/or which do not directly mediate the opening of an ion channel in the neuron cell membrane are also within the scope of the term "metabotropic receptors." The stimulation of these receptors is believed to produce neuroprotective and neuron-treating effects as does the stimulation of the metabotropic receptors which have already been investigated.

As further used herein, the term "ACPD" denotes the two enantiomers of ACPD which are known to specifically stimulate the metabotropic glutamate receptors. These forms are trans-ACPD and 1S,3R-ACPD. However, it is to be understood that other agonists which specifically stimulate metabotropic glutamate receptors and do not stimulate ionotropic glutamate receptors can also be used in accomplishing the methods of the present invention. Thus, other specific metabotropic receptor agonists can be used in combination with or in place of ACPD in the present methods.

Also as used herein, the term "pharmacologically effective dose" means a dose of a metabotropic receptor agonist which will treat or protect a subject from a neurodegenerative disease such as Alzheimer's disease. Pharmacologically effective doses of a metabotropic receptor agonist can be determined by one of skill in the art through routine experimentation using animals or through clinical trials in humans. For example, in order to determine a pharmacologically effective dose for treating a subject, a human or animal subject with a particular neurodegenerative condition can be administered a dose of a metabotropic receptor agonist. If that subject shows improvement compared to a similar subject who is not given the metabotropic receptor agonist, then the administered dose is a pharmacologically effective dose for the treatment of the neurodegenerative condition.

A pharmacologically effective dose for the purpose of protecting a subject from a neurodegenerative condition and preventing the subject from contracting the condition can be similarly determined. In this case, a dose of a metabotropic receptor agonist is first administered to some randomly selected experimental animals out of a group of such animals. A neurodegenerative condition is then induced in all of the animals in this group, and the extent of neurodegeneration in the animals to whom the metabotropic receptor agonist was administered is compared to the amount of neurodegeneration in animals which received no metabotropic receptor agonist. If those animals which received the agonist experience less neurodegeneration, then the dose of the metabotropic receptor agonist administered to such animals is a pharmacologically effective dose. Further examples of how to determine a pharmacologically effective dose are given below.

1. Use of Metabotropic Agongists In Vitro

We have shown that neurons can be protected from β-amyloid induced toxicity in vitro through the administration of the metabotropic receptor agonist ACPD. In one experiment, embryonic rat hippocampal neurons removed from 18 day old fetal rats were cultured (as described in Brewer, G. L. and Cotman, C. W., *Survival and growth of hippocampal neurons in defined medium at low density: Advantages of a sandwich culture technique or low oxygen, Brain Res.*, 494:65–74 (1989)) and plated in 15.5 mm wells (250,000–350,000 cells/well) in Dulbecco's modified Eagle's medium (DME, supplied by Irvine Scientific). These neurons were exposed to β-amyloid peptide 25–35, a synthetic β-amyloid protein comprising 11 amino acids of the β-amyloid protein which occurs in senile plaques in the human brain.

The cultured neurons were exposed to either β-amyloid peptide 25–35 alone or in combination with ACPD for 48 hours. At the end of this time the culture media was assayed for lactate dehydrogenase (LDH), which is released by damaged and dying neurons. The results of this assay are shown in FIG. 1, which shows that in the presence of ACPD the amount of LDH released in response to β-amyloid exposure is markedly lower than that observed when the cultures are treated with β-amyloid alone. Thus, less neuronal damage and death occurs when neurons are exposed to β-amyloid in the presence of ACPD. In fact, in this experiment, the levels of LDH released by the cultured neurons in the presence of β-amyloid and at least 10 μM ACPD were not significantly different from the levels of LDH released by neurons in a control group which were not treated with either β-amyloid or ACPD.

The inhibition of β-amyloid-induced neuronal damage by ACPD in the foregoing experiment is consistent with the concentrations of ACPD known to be required to occupy all of the metabotropic receptors of the cultured neurons. Although the mechanism by which ACPD protects neurons has not been completely elucidated, it is believed that by stimulating metabotropic receptors, ACPD initiates a cascade of intracellular reactions which enable the cell to return to or maintain a normal homeostasis in the presence of the β-amyloid protein.

2. Use of Metabotropic Agonists In Vivo

In addition to in vitro uses of metabotropic receptor agonists, the present invention also includes methods of treating or preventing neurodegenerative diseases in vivo with such agonists. For example, progressive neurodegenerative diseases, particularly those associated with β-amyloid deposition such as Alzheimer's disease (AD), Down's Syndrome, and HIV Neuropathy, can be prevented or treated by administering a pharmacologically effective dose of metabotropic receptor agonist to a subject mammal which is afflicted with one of these diseases or which exhibits one or more of the indicia of these diseases. Since the neurotoxic effects of β-amyloid appear to be at least a contributive cause of Alzheimer's disease if not the major reason for the neurodegeneration associated with that disease, some or all of the neurodegeneration associated with Alzheimer's disease can be halted, and the neurological functioning of a patient with AD can be improved, by administering a pharmacologically effective dose of a metabotropic receptor agonist such as ACPD to a subject mammal which is diagnosed as having Alzheimer's disease.

AD can be diagnosed by a qualified individual, such as a physician, who observes and correlates indicia of AD according to accepted diagnostic criteria. Indicia of AD include a family history of the disease, external symptoms such as dementia and characteristic behavior patterns, and the presence or absence of biochemical or immunological indicators, such as the amyloid precursor protein (APP). Low levels of APP in the cerebrospinal fluid (CSF) of an individual (as determined by an antibody test) compared to the levels in non-AD individuals are indicative of AD. See Van Nostrand et al., *Science*, 256:1279 (1992).

A subject who is at risk for contracting AD or another neurodegenerative disease associated with β-amyloid toxicity can also be treated with a metabotropic receptor agonist in order to prevent or substantially prevent this disease. Such a subject is one which exhibits one or some indicia of Alzheimer's disease, such as dementia or a family history of the disease, but which does not exhibit enough indicia to warrant a diagnosis of AD. For example, since Down's Syndrome has been linked with Alzheimer's-like plaque formation, someone with Down's syndrome has the necessary indicia to be at risk for developing AD or an AD-like syndrome. Such a subject, as well as other subjects who exhibit indicia of AD and are thus at risk for coming down with this disease, can be administered a dose of a metabotropic agonist which is pharmacologically effective for preventing AD.

Since other neurodegenerative diseases can be exacerbated if not necessarily solely caused by β-amyloid toxicity, these diseases can also be treated or prevented through the administration of metabotropic receptor agonists. For example, a person suffering from neurodegeneration due to Parkinson's disease can benefit from the administration of metabotropic receptor agonists. These agonists will treat and protect against any damage done to the neurons of individuals with Parkinson's disease or other progressive neurodegenerative diseases by the β-amyloid protein, and thus will help to improve the neurological conditions of such individuals. Other neurodegenerative diseases which can be treated or prevented through the administration of metabotropic receptor agonists include ALS (Lou Gehrig's Disease), Huntington's Disease, Multiple Infarct Dementia, and Transigent Ischemic Attacks (TIA).

Subjects who exhibit one or some indicia of the foregoing diseases, such as having observable symptoms or a biochemical indicator of one of these diseases, can be administered a metabotropic agonist. Those who are definitively diagnosed as having one of these disease can be treated with a pharmacologically effective dose of a metabotropic receptor agonist for treating a neurodegenerative disease. Those, however, who exhibit only one or some of the indicia associated with these diseases and who are thus only at risk for contracting one of the foregoing diseases can be administered a dose of a metabotropic agonist which is pharmacologically effective for preventing a neurological disease.

3. Metabotropic Agonists

Compounds useful in the present invention include compounds which selectively stimulate a metabotropic receptor.

Examples include trans-ACPD (aminocyclopentane-trans 1,3-dicarboxylic acid) and 1S,3R-ACPD. Compounds such as these which stimulate metabotropic receptors without activating non-metabotropic glutamate receptors are preferred in the present invention.

Other compounds which activate metabotropic receptors, such as quisqualate and ibotenate, are also known. These agonists, however, appear to stimulate glutamate receptors which are linked to ion channels in the neuron cell membrane in addition to stimulating metabotropic receptors. Compounds which stimulate ionotropic glutamate receptors in addition to metabotropic receptors can be made more effective, however, by administering antagonists of the ionotropic receptors which are stimulated by such compounds at the same time that these compounds are administered. For example, ibotenate can be more effectively used according to the present invention if it is administered with AP5 ($\alpha$-5-phosphorovalerate), an NMDA receptor antagonist. The ibotenate in this combination is administered in a dose in the range of between 0.01 and 6,000 mg/kg, while the AP5 is administered in the range of between 0.001 and 2,000 mg/kg. The combination would be administered if a subject has built up an immunity to or is allergic to other, more selective metabotropic agonists.

Compounds useful in the present invention for preventing cell damage caused by $\beta$-amyloid can be selected by assaying such compounds for their ability to prevent the death of cultured neurons following treatment with $\beta$-amyloid peptides. Similarly, compounds useful in treating neurodegeneration caused by $\beta$-amyloid proteins can be selected by assaying such compounds for their ability to improve the physical condition of neurons damaged by $\beta$-amyloid. The physical condition of neurons can be assessed, for example, by measuring the amount of LDH which is given off by the neurons being tested. An increase in the amount of LDH released by a neuron or group of neurons compared to a control group of neurons indicates that the neurons are dying or becoming more damaged, while a lower amount of LDH release indicates that such cells are healthy or protected from injury.

Compounds useful in the present invention can also be selected by identifying compounds which bind to metabotropic glutamate receptors, or which stimulate the second messenger systems associated with metabotropic receptors. Other useful compounds include those which induce long-lasting, desensitizing depolarizations of neurons.

4. Administration of Metabotropic Receptor Agonists

Metabotropic receptor agonists can be administered in any way known to those of skill in the art. For example, these compounds can be administered orally, parenterally, or intravenously. In some cases, agonists within the scope of the invention may be too easily degraded in vivo or may be unable to cross the blood brain barrier. In such cases, alternate routes of administration may be preferred. For example, such compounds can be directly administered to an affected area of tissue via a catheter. When using a catheter to administer metabotropic receptor agonists, the compounds can be infused through the catheter directly to the neurons at the affected site. Alternatively, the compounds can be administered by infusing them into the cerebrospinal fluid (CSF).

The amount of metabotropic agonist administered according to the methods of the present invention will vary greatly from compound to compound, depending of course on the activity of the compound, the route of administration, the rate at which it is degraded in vivo, and other factors which are known to those of skill in the art or which can be determined by routine experimentation. Preferably, an amount of metabotropic agonist is administered which is sufficient to occupy some or all of the metabotropic receptor sites of the neurons which are experiencing damage or which are susceptible to being damaged due to $\beta$-amyloid toxicity or other causes. Lower dosages can also be administered according to the methods of the present invention.

In general, a pharmacologically effective dose of a metabotropic receptor agonist, both for treating a neurodegenerative condition and for preventing or protecting against such a condition, will be in the range of about 0,001 to 100 mg/kg, and preferably within the range of about 0.1 to 10 mg/kg. When the agonist is trans-ACPD, a pharmacologically effective dose will be in the range of approximately 0.1 to 50 mg/kg, and preferably in the range of 0.2 mg/kg to 10 mg/kg.

In order to determine a dose of a metabotropic receptor agonist which is pharmacologically effective in treating a human or other mammalian subject with a particular neurodegenerative disease or condition, a subject having such a condition is first selected. That subject is then administered a predetermined dose of a metabotropic receptor agonist. If that subject shows improvement, such as improved neurological ability or greater motor control, compared to a control subject who also has the neurodegenerative condition but who is not administered the predetermined dose of the metabotropic receptor agonist, then the predetermined dose is a pharmacologically effective dose for the treatment of the neurodegenerative condition.

A pharmacologically effective dose of a metabotropic receptor agonist for preventing a subject from contracting a neurodegenerative condition can be determined by first selecting an animal subject which can be induced to develop the condition. A predetermined dose of a metabotropic receptor agonist is then administered to approximately half of the subjects in a randomly selected group of such subject animals. After this, a neurodegenerative condition is induced in all of the subjects in this group, and the extent of neurodegeneration in the subjects to whom the metabotropic receptor agonist was administered is compared to the amount of neurodegeneration in the subjects which received no metabotropic receptor agonist. If the subjects which received the agonist experience less neurodegeneration, then the predetermined dose of the metabotropic receptor agonist administered to those subjects is a pharmacologically effective dose.

Long-term studies can also be conducted on human subjects in order to determine a dose of a metabotropic receptor agonist that is pharmacologically effective to prevent a neurodegenerative condition or disease. Human subjects at risk for developing a particular neurodegenerative condition are first chosen according to accepted diagnostic criteria. Such subjects can, for example, exhibit one or more symptoms or other indicia of the neurodegenerative condition. A randomly selected subgroup of these subjects is administered a predetermined dose of a metabotropic receptor agonist for a period of years prior to the time such subjects would be expected to develop the neurodegenerative condition based on the indicia they exhibit, while the rest of the subjects are administered a placebo over this period of time. If the subjects receiving the predetermined dose of the metabotropic receptor agonist experience less degeneration compared to the subjects receiving placebos, then the predetermined dose is a pharmacologically effective dose for preventing or substantially preventing the neurodegenerative condition.

A greater appreciation of the scope and utility of the present invention can be obtained by reference to the following examples:

EXAMPLE 1

Inhibition of β-Amyloid Toxicity in Hippocampal Neurons by ACPD

Embryonic rat hippocampal neurons were cultured as described in Brewer, G. L. and Cotman, C. W., *Survival and growth of hippocampal neurons in defined medium at low density: Advantages of a sandwich culture technique at low oxygen. Brain Res.*, 494:65–74 (1989). The neurons were exposed to either β-amyloid peptide 25–35 alone or in combination with ACPD for 48 hours. At the end of this time the culture media was assayed for LDH. FIG. 1 shows that in the presence of ACPD the amount of LDH released in response to β-amyloid exposure is lower than that observed when cultures are treated with β-amyloid alone, indicating less neuronal death. The inhibition of β-amyloid-induced neuronal death by ACPD is consistent with the concentrations of ACPD known to be required to occupy the metabotropic receptor.

EXAMPLE 2

Administration of ACPD to Treat Alzheimer's Disease

A patient having late stage Alzheimer's disease is administered 1 mg/kg ACPD in phosphate buffered saline intravenously on a daily basis. The patient's neurological functioning improves after a course of treatment.

EXAMPLE 3

Administration of ACPD to Prevent or Lessen the Severity of the Onset of Alzheimer's Disease A patient who has been determined to be at risk for contracting Alzheimer's disease and who has at least one of the indicia of this disease is administered 5 mg/kg of ACPD orally three times a week. The patient does not develop AD.

EXAMPLE 4

Administration of ACPD to Treat HIV Neuropathy

A patient who carries the HIV virus and is diagnosed as having HIV Neuropathy is administered 1 mg/kg ACPD in phosphate buffered saline intravenously on a daily basis. The patient's neurological functions improve after a course of treatment.

EXAMPLE 5

Administration of ACPD to Prevent or Lessen the Severity of HIV Neuropathy

A patient who has been diagnosed as carrying the HIV virus and who thus is at risk for developing HIV Neuropathy is administered 5 mg/kg of ACPD orally three times a week. The patient does not develop HIV neuropathy.

EXAMPLE 6

Administration of ACPD to Treat ALS

A patient who is diagnosed as having ALS is administered 1 mg/kg ACPD in phosphate buffered saline intravenously on a daily basis. The patient's motor control improves.

EXAMPLE 7

Administration of ACPD to Prevent or Lessen the Severity of ALS

A patient who has been diagnosed as carrying the gene associated with ALS and who thus is at risk for developing ALS is administered 5 mg/kg of ACPD orally three times a week. The patient's motor control does not deteriorate as quickly as it would without the treatment.

EXAMPLE 8

Administration of ACPD to Treat Huntington's Disease

A patient who is diagnosed as having Huntington's Disease is administered 1 mg/kg ACPD in phosphate buffered saline intravenously on a daily basis. The patient's motor control improves.

EXAMPLE 9

Administration of ACPD to Prevent or Lessen the Severity of Huntington's Disease A patient who has been diagnosed as carrying the gene associated with Huntington's Disease and who thus is at risk for developing Huntington's Disease is administered 5 mg/kg of ACPD orally three times a week. The patient's motor control does not deteriorate as quickly as it would without taking ACPD.

EXAMPLE 10

Administration of ACPD to Treat Multiple Infarct Dementia

A patient who is diagnosed as having dementia due to multiple infarctions is administered 1 mg/kg ACPD in phosphate buffered saline intravenously on a daily basis. The patient's neurological functions improve after a course of treatment.

EXAMPLE 11

Administration of ACPD to Prevent or Lessen the Severity of Multiple Infarct Dementia A patient who is diagnosed as being at risk for developing Multiple Infarct Dementia is administered 5 mg/kg of ACPD orally three times a week. The patient does not develop dementia.

EXAMPLE 12

Administration of ACPD to Treat Parkinson's Disease

A patient diagnosed as having Parkinson's Disease is administered 1 mg/kg ACPD in phosphate buffered saline intravenously on a daily basis. The patient's motor control improves after a course of treatment.

EXAMPLE 13

Administration of ACPD to Prevent or Lessen the Severity of the Onset of Parkinson's Disease A patient who has been determined to be at risk for contracting Parkinson's Disease is administered 5 mg/kg of ACPD orally three times a week. The patient's motor control does not deteriorate as rapidly as in the absence of taking ACPD.

EXAMPLE 14

Selecting Compounds Useful in Preventing Neurodegeneration

Analogs of glutamate, aspartate, or any other known activator of glutamate receptors, including other compounds suspected of having a three dimensional conformation which can activate a glutamate receptor, are screened as follows in order to determine whether they are effective in preventing neurodegeneration. Stable cultures of hippocampal neurons are seeded in 24 well plates (provided by Falcon) in Dulbecco.'s modified Eagle's medium. Each of such neuron cultures is then exposed to different doses of one of the aforementioned compounds for one hour, after which the cultures are exposed to 1-42 β-amyloid protein (the form of β-amyloid associated with AD which is found in plaques in human brains) or β-amyloid peptide 25–35 in the continuous presence of the analog or other compound.

After 24 hours of exposure, the neuron cultures are observed, and the LDH content of the neuron cultures is determined. If the appearance and LDH content of any of the cultures treated with a dose of one of the compounds indicates less damage to the neurons compared to a similar culture which was not treated with any compound, then the compound is effective in protecting against the harmful effects to neurons of β-amyloid exposure, and is thus useful in the methods of the present invention.

EXAMPLE 15

Selecting Compounds Useful in Treating Neurodegeneration

Analogs of glutamate, aspartate, or any other known activator of glutamate receptors, including other compounds suspected of having a three dimensional conformation which can activate a glutamate receptor, can also be screened in order to determine whether they have the ability to treat neurodegeneration which already exists. Stable cultures of an HT-4 neuron cell line are first transferred into 96 well plates (provided by Falcon) in DME medium. Then, each of the neuron cultures is exposed to sufficient quisqualate or glutamate and β-amyloid protein for 24 hours to damage but not kill many of the cells. Different doses of one of the aforementioned analogs or compounds is then administered to the cultures for 24 hours.

After 24–48 hours of exposure, the neuron cultures are observed, and the LDH content of the neuron cultures is determined. If the appearance and LDH content of any of the cultures treated with a dose of one of the compounds indicates less damage to the neurons compared to a similar culture which was not treated with any compound, then the compound is effective in treating the harmful effects to neurons of β-amyloid exposure.

EXAMPLE 16

Administration of a Non-Selective Metabotropic Agonist to Treat a Neurodegenerative Disease A subject having late stage Alzheimer's disease is administered a solution of ibotenate and AP5 (β-5-phosphorovalerate) containing approximately 10 mg/kg ibotenate and about 10 mg/kg AP5 in phosphate buffered saline. This solution is administered intravenously on a daily basis. Following treatment, the neurological functions of the subject improve.

The foregoing specific examples of different embodiments of the present invention have been set forth as illustrations of the present invention and not as limitations on its scope. Thus, the true scope of the invention is to be determined with reference to the claims and the entire specification. In addition, the disclosures of the references cited herein which are relied upon to describe certain aspects of the present invention are hereby incorporated by reference.

What is claimed is:

1. A method of treating a mammal with a neurodegenerative disease which is caused at least in part by β-amyloid protein neurotoxicity, comprising administering to said mammal a pharmacologically effective dose of a metabotropic receptor agonist.

2. The method of claim 1, comprising administering to said mammal a pharmacologically effective dose of an agent which acts selectively as an agonist at a metabotropic receptor and not at a receptor in the ionotropic class of glutamate receptors.

3. The method of claim 2, comprising administering a pharmacologically effective dose of ACPD to said mammal.

4. The method of claim 1, comprising administering a pharmacologically effective dose of ibotenate to said mammal.

5. The method of claim 1, comprising administering said metabotropic receptor agonist to a mammal which has Parkinson's disease.

6. The method of claim 1, comprising administering said metabotropic receptor agonist to a mammal which has Alzheimer's disease.

7. A method of preventing a neurodegenerative disease in a mammal which has at least one indicium of said disease, wherein said disease is caused at least in part by the neurotoxic effects of the β-amyloid protein, comprising administering a pharmacologically effective dose of a metabotropic receptor agonist to said mammal.

8. The method of claim 7, comprising administering a pharmacologically effective dose of an agent which acts selectively as an agonist at a metabotropic receptor and not at a receptor in the ionotropic class of glutamate receptors.

9. The method of claim 8, comprising administering a pharmacologically effective dose of ACPD to said mammal.

10. The method of claim 7, comprising administering a pharmacologically effective dose of ibotenate to said mammal.

11. The method of claim 7, comprising administering said metabotropic receptor agonist to a mammal which is at risk for developing Parkinson's disease.

12. The method of claim 7, comprising administering said metabotropic receptor agonist to a mammal which is at risk for developing Alzheimer's disease.

13. A method of inhibiting cellular damage in nervous system cells exposed to β-amyloid protein, comprising contacting said cells with a dose of a metabotropic receptor agonist which is effective in preventing or treating damage to said cells wherein said damage is caused at least in part by the exposure to β-amyloid protein.

14. The method of claim 13, wherein said cells are mammalian nervous system cells.

15. The method of claim 13, further comprising the step of treating said nervous system cells in vivo.

16. The method of claim 13, further comprising the step of treating said nervous system cells in vitro.

17. The method of claim 13, wherein said agonist is ACPD.

18. The method of claim 13, wherein said agonist is ibotenate.

* * * * *